(12) United States Patent
Ueda et al.

(10) Patent No.: US 11,642,053 B2
(45) Date of Patent: May 9, 2023

(54) MEDICAL PHOTOMETER AND MEDICAL PHOTOMETRY SYSTEM

(71) Applicant: NIHON KOHDEN CORPORATION, Tokyo (JP)

(72) Inventors: Yoshinori Ueda, Tokorozawa (JP);
Naoki Kobayashi, Tokorozawa (JP);
Kazumasa Ito, Tokorozawa (JP);
Hideki Fujisaki, Tokorozawa (JP);
Teiji Ukawa, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1060 days.

(21) Appl. No.: 16/134,539

(22) Filed: Sep. 18, 2018

(65) Prior Publication Data

US 2019/0083016 A1 Mar. 21, 2019

(30) Foreign Application Priority Data

Sep. 20, 2017 (JP) .............................. JP2017-180016

(51) Int. Cl.
*A61B 5/1455* (2006.01)
*A61B 5/00* (2006.01)
*A61M 16/00* (2006.01)

(52) U.S. Cl.
CPC ........ *A61B 5/14552* (2013.01); *A61B 5/0053* (2013.01); *A61M 16/024* (2017.08);
(Continued)

(58) Field of Classification Search
CPC ...... A61M 2230/005; A61M 2230/205; A61M 2202/0208; A61B 5/0261; A61B 5/02416; A61B 5/14551
See application file for complete search history.

(56) References Cited

U.S. PATENT DOCUMENTS

| | | |
|---|---|---|
| 2003/0236452 A1 | 12/2003 | Melker et al. |
| 2004/0230108 A1 | 11/2004 | Melker et al. |
| (Continued) | | |

FOREIGN PATENT DOCUMENTS

| | | |
|---|---|---|
| EP | 2813180 A1 | 12/2014 |
| EP | 3135198 A1 | 3/2017 |
| (Continued) | | |

OTHER PUBLICATIONS

Communication dated Apr. 13, 2021, from the Japanese Patent Office in Application No. 2017-180016.

(Continued)

*Primary Examiner* — Nathan J Jenness
*Assistant Examiner* — Michael A Catina
(74) *Attorney, Agent, or Firm* — Sughrue Mion, PLLC (57) ABSTRACT

A medical photometer includes a signal producing section that produces a first control signal to emit a first light having a first wavelength, a second control signal to emit a second light having a second wavelength, a third control signal to emit a third light having a third wavelength, and a fourth control signal to emit a fourth light having a fourth wavelength, a signal acquiring section that acquires a first to fourth intensity signals, a processor, and a memory that stores instructions. In the medical photometer, the first wavelength and the second wavelength are selected as two wavelengths at each of which an extinction coefficient of blood is a first value. The third wavelength and the fourth wavelength are selected as two wavelengths at each of which the extinction coefficient of the blood is a second value which is different from the first value.

4 Claims, 3 Drawing Sheets

(52) U.S. Cl.
CPC ... *A61B 2562/0238* (2013.01); *A61B 2562/04* (2013.01); *A61M 2202/0208* (2013.01); *A61M 2205/3313* (2013.01); *A61M 2230/205* (2013.01)

(56) References Cited

U.S. PATENT DOCUMENTS

| | | |
|---|---|---|
| 2004/0260161 A1 | 12/2004 | Melker et al. |
| 2004/0267140 A1 | 12/2004 | Ito et al. |
| 2005/0049469 A1* | 3/2005 | Aoyagi ............... A61B 5/14551 600/323 |
| 2007/0027375 A1 | 2/2007 | Melker et al. |
| 2008/0058621 A1 | 3/2008 | Melker et al. |
| 2010/0121314 A1* | 5/2010 | Lobbi ............... A61M 16/0051 604/890.1 |
| 2010/0192952 A1 | 8/2010 | Melker et al. |
| 2010/0280343 A1 | 11/2010 | Huiku |
| 2012/0078069 A1 | 3/2012 | Melker |
| 2014/0094670 A1 | 4/2014 | Melker et al. |
| 2014/0155704 A1 | 6/2014 | Melker et al. |
| 2014/0155713 A1 | 6/2014 | Melker et al. |
| 2014/0158132 A1 | 6/2014 | Melker |
| 2014/0180026 A1 | 6/2014 | Melker et al. |
| 2014/0213865 A1 | 7/2014 | Kobayashi et al. |
| 2014/0243630 A1 | 8/2014 | Melker et al. |
| 2014/0243631 A1 | 8/2014 | Melker |
| 2014/0371557 A1* | 12/2014 | Kobayashi ......... A61B 5/14552 600/328 |
| 2017/0238871 A1 | 8/2017 | Melker |
| 2018/0008155 A1 | 1/2018 | Melker et al. |
| 2018/0049654 A1 | 2/2018 | Melker et al. |

FOREIGN PATENT DOCUMENTS

| | | |
|---|---|---|
| JP | 2004-148070 A | 5/2004 |
| JP | 2005-95581 A | 4/2005 |
| JP | 2007-218480 A | 7/2007 |
| JP | 2007-518480 A | 7/2007 |
| JP | 4196209 B2 | 12/2008 |
| JP | 2014-147473 A | 8/2014 |
| JP | 2015-127 A | 1/2015 |
| WO | 2015/038852 A1 | 3/2015 |

OTHER PUBLICATIONS

Communication dated Jan. 3, 2019, issued by the European Patent Office in counterpart European Patent Application No. 18195381.1.

* cited by examiner

MEDICAL PHOTOMETER AND MEDICAL PHOTOMETRY SYSTEM

CROSS REFERENCE TO RELATED APPLICATION

This application is based on Japanese Patent Applications No. 2017-180016 filed on Sep. 20, 2017, the contents of which are incorporated herein by reference.

BACKGROUND

The presently disclosed subject matter relates to a medical photometer, and a medical photometry system including the medical photometer.

Japanese Patent No. 4,196,209 discloses a pulse photometer which is an example of a medical photometer. A pulse photometer is a device for calculating the arterial oxygen saturation of a subject as an example of the photometry. Specifically, the tissue of the subject is irradiated with light beams respectively having a plurality of wavelengths at which ratios of the extinction coefficients of the blood are different from each other. The quantities of the light beams of the respective wavelengths which are transmitted through or reflected from are detected. The quantities of the light beams of the respective wavelengths are changed in accordance with the pulsation of the blood of the subject.

Therefore, temporal changes of the quantities of the light beams of the respective wavelengths are acquired as pulse wave signals. The amplitude of the pulse wave signal relating to each of the wavelengths corresponds to the light attenuation variation at the wavelength. The arterial oxygen saturation is calculated based on a ratio of the light attenuation variations at the wavelengths.

Recently, it has been known that excessive administration of oxygen to a subject imposes a burden on the subject. In accordance with administration of oxygen, the arterial oxygen saturation in the blood of the subject is increased. Namely, the arterial oxygen saturation can be used as an index of knowing the level of administration of oxygen to the subject. When the arterial oxygen saturation reaches 100%, however, it is difficult to determine whether administration of oxygen is excessive.

A novel index which, when the arterial oxygen saturation of a subject is 100%, enables to determine whether the amount of administration of oxygen to the subject is adequate is provided.

SUMMARY

According to an aspect of the presently disclosed subject matter, a medical photometer includes:
a signal producing section that produces:
a first control signal that causes a first light emitter to emit a first light beam having a first wavelength;
a second control signal that causes a second light emitter to emit a second light beam having a second wavelength;
a third control signal that causes a third light emitter to emit a third light beam having a third wavelength; and
a fourth control signal that causes a fourth light emitter to emit a fourth light beam having a fourth wavelength;
a signal acquiring section that acquires:
a first intensity signal corresponding to an intensity of the first light beam which is transmitted through or reflected from tissue of a subject;
a second intensity signal corresponding to an intensity of the second light beam which is transmitted through or reflected from the tissue;
a third intensity signal corresponding to an intensity of the third light beam which is transmitted through or reflected from the tissue; and
a fourth intensity signal corresponding to an intensity of the fourth light beam which is transmitted through or reflected from the tissue;
a processor; and
a memory that stores instructions executable by the processor,
wherein the first wavelength and the second wavelength are selected as two wavelengths at each of which an extinction coefficient of blood in a state where an oxygen saturation is 100% is a first value,
the third wavelength and the fourth wavelength are selected as two wavelengths at each of which the extinction coefficient of the blood in a state where the oxygen saturation is 100% has a second value which is different from the first value, and,
when the instructions are executed by the processor, a venous oxygen saturation in a state where an arterial oxygen saturation of the subject is 100% is calculated based on the first control signal, the second control signal, the third control signal, the fourth control signal, the first intensity signal, the second intensity signal, the third intensity signal, and the fourth intensity signal.

According to another aspect of the presently disclosed subject matter, a medical photometry system includes:
a first light emitter that emits a first light beam having a first wavelength;
a second light emitter that emits a second light beam having a second wavelength;
a third light emitter that emits a third light beam having a third wavelength;
a fourth light emitter that emits a fourth light beam having a fourth wavelength;
a light detector that outputs a first intensity signal corresponding to an intensity of the first light beam that is transmitted through or reflected from tissue of a subject, a second intensity signal corresponding to an intensity of the second light beam that is transmitted through or reflected from the tissue, a third intensity signal corresponding to an intensity of the third light beam that is transmitted through or reflected from the tissue, and a fourth intensity signal corresponding to an intensity of the fourth light beam that is transmitted through or reflected from the tissue; and
a medical photometer to which the first light emitter, the second light emitter, the third light emitter, the fourth light emitter, and the light detector are connected with wire or wireless connection,
wherein the medical photometer includes:
a signal producing section that produces a first control signal that causes the first light emitter to emit the first light beam, a second control signal that causes the second light emitter to emit the second light beam, a third control signal that causes the third light emitter to emit the third light beam, and a fourth control signal that causes the fourth light emitter to emit the fourth light beam;
a signal acquiring section that acquires the first intensity signal, the second intensity signal, the third intensity signal, and the fourth intensity signal;
a processor; and
a memory that stores instructions executable by the processor, the first wavelength and the second wavelength are selected as two wavelengths at each of which an extinction coefficient of blood in a state where an oxygen saturation is 100% has a first value, the third wavelength and the fourth wavelength are selected as two wavelengths at each of which the extinction coefficient of the blood in a state where the oxygen saturation is 100% has a second value that is different from the first value, and, when the instructions are executed by the processor, a venous oxygen saturation in a state where an arterial oxygen saturation of the subject is 100% is calculated based on the first control signal, the second control signal, the third control signal, the fourth control signal, the first intensity signal, the second intensity signal, the third intensity signal, and the fourth intensity signal.

According to another aspect of the presently disclosed subject matter, a medical photometer includes:

a signal acquiring section that acquires:

a first intensity signal corresponding to an intensity of a first light beam which is transmitted through or reflected from tissue of a subject, and which has a first wavelength;

a second intensity signal corresponding to an intensity of a second light beam which is transmitted through or reflected from the tissue, and which has a second wavelength;

a third intensity signal corresponding to an intensity of a third light beam which is transmitted through or reflected from the tissue, and which has a third wavelength; and a fourth intensity signal corresponding to an intensity of a fourth light beam which is transmitted through or reflected from the tissue, and which has a fourth wavelength;

a processor; and a memory that stores instructions executable by the processor, wherein the first wavelength and the second wavelength are selected as two wavelengths at each of which an extinction coefficient of blood in a state where an oxygen saturation is 100% has a first value, the third wavelength and the fourth wavelength are selected as two wavelengths at each of which the extinction coefficient of the blood in a state where the oxygen saturation is 100% has a second value that is different from the first value, and, when the instructions are executed by the processor, the medical photometer acquires a first signal set including the first intensity signal, second intensity signal, third intensity signal, and fourth intensity signal in a state where the tissue is not pressurized, acquires a second signal set including the first intensity signal, second intensity signal, third intensity signal, and fourth intensity signal in a state where the tissue is pressurized, and calculates a venous oxygen saturation in a state where an arterial oxygen saturation of the subject is 100%, based on the first signal set and the second signal set.

According to another aspect of the presently disclosed subject matter, a medical photometry system includes:

a first light emitter that emits a first light beam having a first wavelength;

a second light emitter that emits a second light beam having a second wavelength;

a third light emitter that emits a third light beam having a third wavelength;

a fourth light emitter that emits a fourth light beam having a fourth wavelength;

a light detector that outputs a first intensity signal corresponding to an intensity of the first light beam that is transmitted through or reflected from tissue of a subject, a second intensity signal corresponding to an intensity of the second light beam that is transmitted through or reflected from the tissue, a third intensity signal corresponding to an intensity of the third light beam that is transmitted through or reflected from the tissue, and a fourth intensity signal corresponding to an intensity of the fourth light beam that is transmitted through or reflected from the tissue; and a medical photometer to which the first light emitter, the second light emitter, the third light emitter, the fourth light emitter, and the light detector are connected with wire or wireless connection, wherein the medical photometer includes:

a signal acquiring section that acquires the first intensity signal, the second intensity signal, the third intensity signal, and the fourth intensity signal;

a processor; and a memory that stores instructions executable by the processor, the first wavelength and the second wavelength are selected as two wavelengths at each of which an extinction coefficient of blood in a state where an oxygen saturation is 100% has a first value.

the third wavelength and the fourth wavelength are selected as two wavelengths at each of which the extinction coefficient of the blood in a state where the oxygen saturation is 100% has a second value that is different from the first value, and, when the instructions are executed by the processor, the medical photometer acquires a first signal set including the first intensity signal, second intensity signal, third intensity signal, and fourth intensity signal in a state where the tissue is not pressurized, acquires a second signal set including the first intensity signal, second intensity signal, third intensity signal, and fourth intensity signal in a state where the tissue is pressurized, and calculates a venous oxygen saturation in a state where an arterial oxygen saturation of the subject is 100%, based on the first signal set and the second signal set.

According to the above-described modes, even when the arterial oxygen saturation of a subject is 100%, it is possible to determine whether the amount of administration of oxygen to the subject is adequate, based on the calculated venous oxygen saturation. In other words, a novel index is provided which, when the arterial oxygen saturation of a subject is 100%, enables to determine whether the amount of administration of oxygen to the subject is adequate.

DETAILED DESCRIPTION OF EMBODIMENTS

Figure 1:
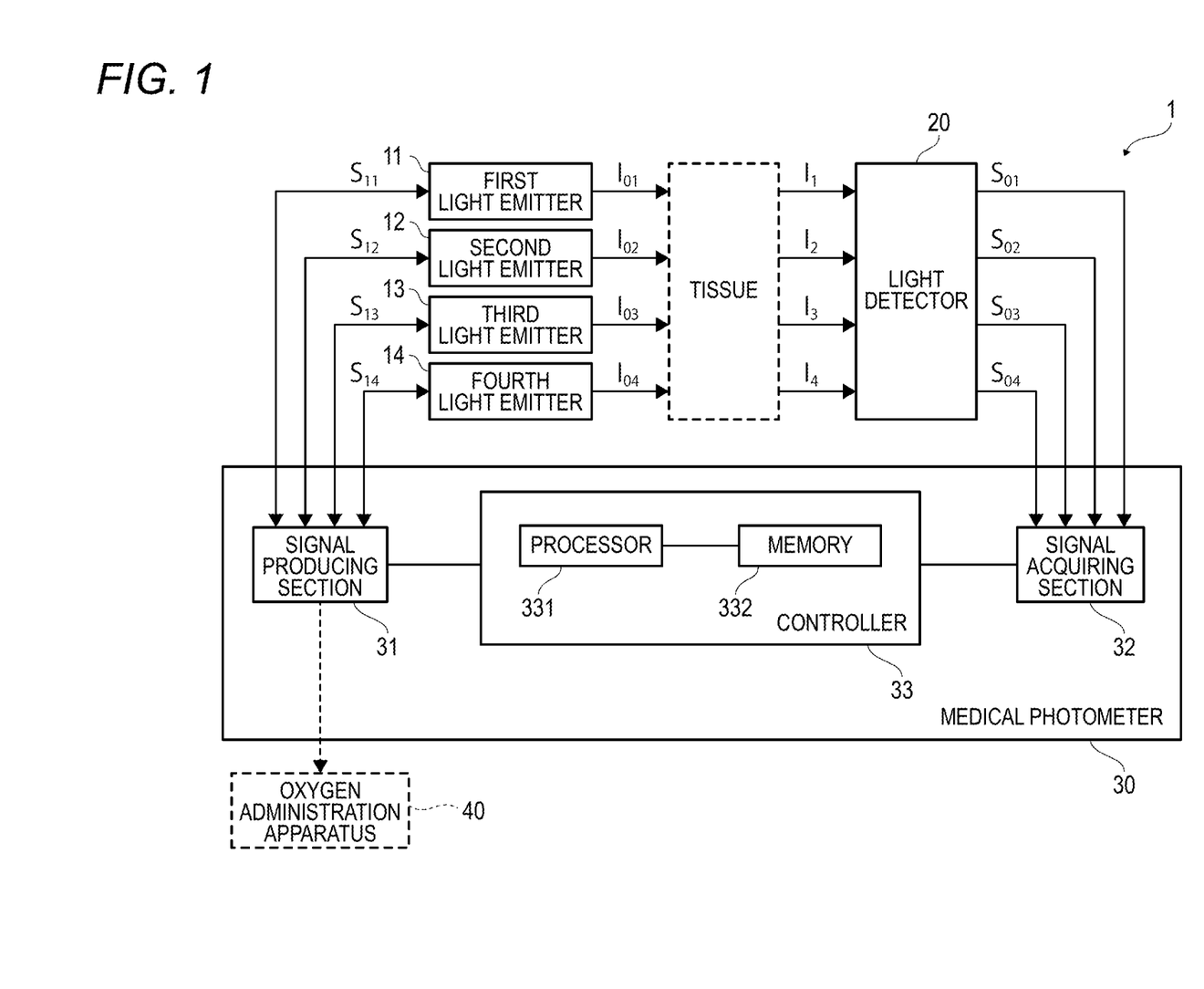
FIG. 1 is a functional diagram illustrating a functional configuration of a medical photometry system of an embodiment.

Hereinafter, an embodiment will be described in detail with reference to the accompanying drawings. FIG. 1 illustrates the functional configuration of a medical photometry system 1 of the embodiment.

The medical photometry system 1 includes a first light emitter 11, a second light emitter 12, a third light emitter 13, a fourth light emitter 14, a light detector 20, and a medical photometer 30.

The first light emitter 11 is configured so as to emit a first light beam having a first wavelength $\lambda_1$. An example of the first wavelength $\lambda_1$ is 660 nm. The first light emitter 11 is a semiconductor light emitting element which emits the first light beam. Examples of the semiconductor light emitting element are a light emitting diode (LED), a laser diode, and an organic electroluminescence (EL) element.

The second light emitter 12 is configured so as to emit a second light beam having a second wavelength $\lambda_2$. An example of the second wavelength $\lambda_2$ is 700 nm. The second light emitter 12 is a semiconductor light emitting element which emits the second light beam. Examples of the semiconductor light emitting element are a light emitting diode (LED), a laser diode, and an organic electroluminescence (EL) element.

The third light emitter 13 is configured so as to emit a third light beam having a third wavelength $\lambda_3$. An example of the third wavelength $\lambda_3$ is 645 nm. The third light emitter 13 is a semiconductor light emitting element which emits the third light beam. Examples of the semiconductor light emitting element are a light emitting diode (LED), a laser diode, and an organic electroluminescence (EL) element.

The fourth light emitter 14 is configured so as to emit a fourth light beam having a fourth wavelength $\lambda_4$. An example of the fourth wavelength $\lambda_4$ is 730 nm. The fourth light emitter 14 is a semiconductor light emitting element which emits the fourth light beam. Examples of the semiconductor light emitting element are a light emitting diode (LED), a laser diode, and an organic electroluminescence (EL) element.

The light detector 20 is an optical sensor having sensitivities to the first wavelength $\lambda_1$, the second wavelength $\lambda_2$, the third wavelength $\lambda_3$, and the fourth wavelength $\lambda_4$. The light detector may be configured so as to further have sensitivities to other wavelengths. Examples of the optical sensor are a photodiode, a phototransistor, and a photoresistor.

The light detector 20 is configured so as to output a first intensity signal $S_{o1}$ corresponding to the intensity $I_1$ of the first light beam which is transmitted through or reflected from tissue of a subject. The fingertip or earlobe of the subject may be used as an example of the tissue. The light detector 20 is configured so as to output a second intensity signal $S_{o2}$ corresponding to the intensity $I_2$ of the second light beam which is transmitted through or reflected from the tissue. The light detector 20 is configured so as to output a third intensity signal $S_{o3}$ corresponding to the intensity $I_3$ of the third light beam which is transmitted through or reflected from the tissue. The light detector 20 is configured so as to output a fourth intensity signal $S_{o4}$ corresponding to the intensity $I_4$ of the fourth light beam which is transmitted through or reflected from the tissue.

The medical photometer 30 has wired or wireless connections to the first light emitter 11, the second light emitter 12, the third light emitter 13, the fourth light emitter 14, and the light detector 20. The medical photometer 30 includes a signal producing section 31, a signal acquiring section 32, and a controller 33.

The signal producing section 31 is configured so as to produce a first control signal $S_{i1}$, a second control signal Sit, a third control signal $S_{i3}$, and a fourth control signal $S_{i4}$. The first control signal $S_{i1}$ causes the first light emitter 11 to emit the first light beam at a first intensity $I_{01}$. The second control signal Sit causes the second light emitter 12 to emit the second light beam at a second intensity $I_{02}$. The third control signal $S_{i3}$ causes the third light emitter 13 to emit the third light beam at a third intensity $I_{03}$. The fourth control signal $S_{i4}$ causes the fourth emitter 14 to emit the fourth light beam at a fourth intensity $I_{04}$. The signal producing section 31 includes a circuit which produces the first control signal $S_{i1}$, the second control signal $S_{i2}$, the third control signal $S_{i3}$, and the fourth control signal $S_{i4}$ in accordance with instructions from the controller 33, and an interface for outputting these signals.

The signal acquiring section 32 is configured so as to acquire the first intensity signal $S_{o1}$, the second intensity signal $S_{o2}$, the third intensity signal $S_{o3}$, and the fourth intensity signal $S_{o4}$ which are output from the light detector 20. The signal acquiring section 32 includes an interface which receives inputs of the first intensity signal $S_{o1}$, the second intensity signal $S_{o2}$, the third intensity signal $S_{o3}$, and the fourth intensity signal $S_{o4}$, and a signal transmission circuit which transmits the signals to the controller 33.

The controller 33 is communicable with the signal producing section 31 and the signal acquiring section 32. The controller 33 can include one or more processor 331 and one or more memory 332.

Examples of the processor 331 include a CPU and an MPU. The memory 332 is configured so as to store instructions which may be executed by the processor 331. Examples of the memory 332 include a ROM which stores various instructions, and a RAM having a work area in which various instructions to be executed by the processor 331 are stored.

When instructions stored in the memory 332 are executed by the processor 331, the medical photometer 30 executes the following process.

The controller 33 causes the signal producing section 31 to produce the first control signal $S_{i1}$. Therefore, the first light emitter 11 emits the first light beam having the first wavelength $\lambda_1$, at the first intensity $I_{01}$. The light detector 20 receives the first light beam which is transmitted through or reflected from the tissue of the subject, and outputs the first intensity signal $S_{o1}$ corresponding to the intensity $I_1$ of the first light beam. The controller 33 causes the signal acquiring section 32 to acquire the first intensity signal $S_{o1}$.

A light attenuation (first light attenuation) $A_1$ of the first light beam by transmission through or reflection from the tissue is acquired based on the first intensity signal $S_{o1}$. The first light attenuation $A_1$ is expressed by the following expression. Namely, the first light attenuation $A_1$ may be acquired based on the first control signal $S_{i1}$ and the first intensity signal $S_{o1}$.

$$A_1 = \ln(I_{01}/I_1) \quad (1)$$

The controller 33 causes the signal producing section 31 to produce the second control signal $S_{i2}$. Therefore, the second light emitter 12 emits the second light beam having the second wavelength $\lambda_2$, at the second intensity $I_{02}$. The light detector 20 receives the second light beam which is transmitted through or reflected from the tissue of the subject, and outputs the second intensity signal $S_{o2}$ corresponding to the intensity $I_2$ of the second light beam. The controller 33 causes the signal acquiring section 32 to acquire the second intensity signal $S_{o2}$.

A light attenuation (second light attenuation) $A_2$ of the second light beam due to transmission through or reflection from the tissue is acquired based on the second intensity signal $S_{o2}$. The second light attenuation $A_2$ is expressed by the following expression. Namely, the second light attenuation $A_2$ may be acquired based on the second control signal $S_{i2}$ and the second intensity signal $S_{o2}$.

$$A_2 = \ln(I_{02}/I_2) \tag{2}$$

The first light attenuation $A_1$ and the second light attenuation $A_2$ may be expressed by the following expressions, respectively:

$$A_1 = (E_{a1} \cdot Hb \cdot D_a + E_{v1} \cdot Hb \cdot D_v + \Sigma_{t1} \cdot D_t) \tag{3}$$

$$A_2 = (E_{a2} \cdot Hb \cdot D_a + E_{v2} \cdot Hb \cdot D_v + \Sigma_{t2} \cdot D_t) \tag{4}$$

In the above expressions, $E_a$ indicates the extinction coefficient (dl g$^{-1}$ cm$^{-1}$) of the arterial blood, $E_v$ indicates the extinction coefficient (dl g$^{-1}$ cm$^{-1}$) of the venous blood, and $\Sigma_t$ indicates the absorption coefficient (cm$^{-1}$) due to tissue other than the blood. The suffix "1" indicates the first light beam, and the suffix "2" indicates the second light beam. Hb indicates the hemoglobin concentration in blood (g dl$^{-1}$), $D_a$ indicates the thickness (cm) of the arterial blood, $D_v$ indicates the thickness (cm) of the venous blood, and $D_t$ indicates the thickness (cm) of the tissue other than the blood.

In Expressions (3) and (4), namely, the first term of the right side corresponds to the extent of contribution of the arterial blood of the subject to the light attenuation, the second term of the right side corresponds to the extent of contribution of the venous blood of the subject to the light attenuation, and the third term of the right side corresponds to the extent of contribution of the tissue of the subject other than the blood to the light attenuation.

Figure 2:
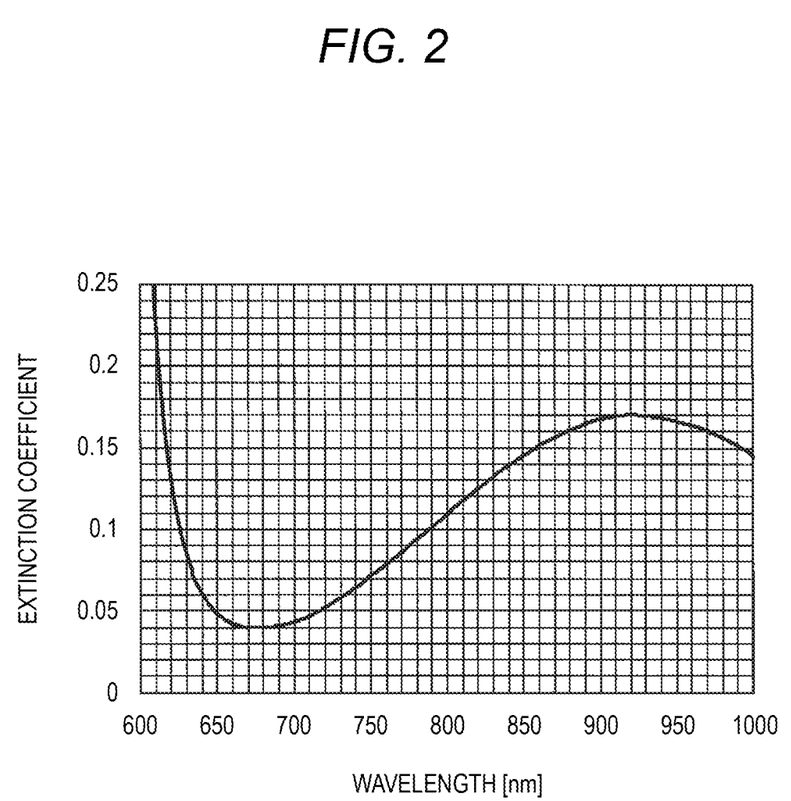
FIG. 2 is a graph for explaining a principle of calculating a venous oxygen saturation.

FIG. 2 illustrates the wavelength dependency of the extinction coefficient of the blood in a state where the oxygen saturation is 100%. In the embodiment, the first wavelength $\lambda_1$ (660 nm) and the second wavelength $\lambda_2$ (700 nm) are selected as two wavelengths at which the extinction coefficients of the blood in a state where the oxygen saturation is 100% have first values that are substantially equal to each other.

Under conditions that the oxygen saturation of the blood of the subject is 100%, namely, $E_{a1}$ and $E_{a2}$ in Expressions (3) and (4) may be deemed to be approximately equal to each other. When also $\Sigma_{t1}$ and $\Sigma_{t2}$ are deemed to be approximately equal to each other, the following expression is obtained:

$$A_1 - A_2 \approx E_{v1} \cdot Hb \cdot D_v - E_{v2} \cdot Hb \cdot D_v = (E_{v1} - E_{v2}) Hb \cdot D_v \tag{5}$$

From Expressions (1) and (2), the left side of Expression (5) may be rewritten as follows:

$$\ln(I_2/I_1) - \ln(I_{02}/I_{01}) = (E_{v1} - E_{v2}) Hb \cdot D_v \tag{6}$$

In Expression (6), the first term of the left side corresponds to the ratio of the first intensity signal $S_{o1}$ and second intensity signal $S_{o2}$ which are acquired by the signal acquiring section 32. The values of $I_{01}$ and $I_{02}$ are already known, and therefore the second term of the left side is constant. When first and second light beams are selected as two beams for which the extinction coefficients of the blood in a state where the oxygen saturation is 100% are substantially equal to each other, namely, it is possible to offset influences on extinction due to the arterial blood and the tissue relating to the first and second light beams.

The controller 33 causes the signal producing section 31 to produce the third control signal $S_{i3}$. Therefore, the third light emitter 13 emits the third light beam having the third wavelength $\lambda_3$, at the third intensity $I_{03}$. The light detector 20 receives the third light beam which is transmitted through or reflected from the tissue of the subject, and outputs the third intensity signal $S_{o3}$ corresponding to the intensity $I_3$ of the third light beam. The controller 33 causes the signal acquiring section 32 to acquire the third intensity signal $S_{o3}$.

A light attenuation (third light attenuation) $A_3$ of the third light beam due to transmission through or reflection from the tissue is acquired based on the third intensity signal $S_{o3}$. The third light attenuation $A_3$ is expressed by the following expression. Namely, the third light attenuation $A_3$ may be acquired based on the third control signal $S_{i3}$ and the third intensity signal $S_{o3}$.

$$A_3 = \ln(I_{03}/I_3) \tag{7}$$

The controller 33 causes the signal producing section 31 to produce the fourth control signal $S_{i4}$. Therefore, the fourth light emitter 14 emits the fourth light beam having the fourth wavelength $\lambda_4$, at the fourth intensity $I_{04}$. The light detector 20 receives the fourth light beam which is transmitted through or reflected from the tissue of the subject, and outputs the fourth intensity signal $S_{o4}$ corresponding to the intensity $I_4$ of the fourth light beam. The controller 33 causes the signal acquiring section 32 to acquire the fourth intensity signal $S_{o4}$.

A light attenuation (fourth light attenuation) $A_4$ of the fourth light beam due to transmission through or reflection from the tissue is acquired based on the fourth intensity signal $S_{o4}$. The fourth light attenuation $A_4$ is expressed by the following expression. Namely, the fourth light attenuation $A_4$ may be acquired based on the fourth control signal $S_{i4}$ and the forth intensity signal $S_{o4}$.

$$A_4 = \ln(I_{04}/I_4) \tag{8}$$

The third light attenuation $A_3$ and the fourth light attenuation $A_4$ may be expressed by the following expressions, respectively:

$$A_3 = (E_{a3} \cdot Hb \cdot D_a + E_{v3} \cdot Hb \cdot D_v + \Sigma_{t3} \cdot D_t) \tag{9}$$

$$A_4 = (E_{a4} \cdot Hb \cdot D_a + E_{v4} \cdot Hb \cdot D_v + \Sigma_{t4} \cdot D_t) \tag{10}$$

In the above expressions, $E_a$ indicates the extinction coefficient (dl g$^{-1}$ cm$^{-1}$) of the arterial blood, $E_v$ indicates the extinction coefficient (dl g$^{-1}$ cm$^{-1}$) of the venous blood, and $\Sigma_t$ indicates the absorption coefficient (cm$^{-1}$) due to tissue other than the blood. The suffix "3" indicates the third light beam, and the suffix "4" indicates the fourth light beam. Hb indicates the hemoglobin concentration in blood (g dl$^{-1}$), $D_a$ indicates the thickness (cm) of the arterial blood, $D_v$ indicates the thickness (cm) of the venous blood, and $D_t$ indicates the thickness (cm) of the tissue other than the blood.

In Expressions (9) and (10), namely, the first term of the right side corresponds to the extent of contribution of the arterial blood of the subject to the light attenuation, the second term of the right side corresponds to the extent of contribution of the venous blood of the subject to the light attenuation, and the third term of the right side corresponds to the extent of contribution of the tissue of the subject other than the blood to the light attenuation.

As illustrated in FIG. 2, the third wavelength $\lambda_3$ (645 nm) and the fourth wavelength $\lambda_4$ (730 nm) are selected as two wavelengths at which the extinction coefficients of the blood in a state where the oxygen saturation is 100% have second values that are substantially equal to each other. The second values are different from the above-described first values.

Under the conditions that the oxygen saturation of the blood of the subject is 100%, namely, $E_{a3}$ and $E_{a4}$ in Expressions (9) and (10) may be deemed to be approximately equal to each other. When also $\Sigma_{t3}$ and $\Sigma_{t4}$ are deemed to be approximately equal to each other, the following expression is obtained:

$$A_3 - A_4 \approx E_{v3} \cdot Hb \cdot D_v - E_{v4} \cdot Hb \cdot D_v = (E_{v3} - E_{v4}) Hb \cdot D_v \quad (11)$$

From Expressions (7) and (8), the left side of Expression (11) may be rewritten as follows:

$$\ln(I_4/I_3) - \ln(I_{04}/I_{03}) = (E_{v3} - E_{v4}) Hb \cdot D_v \quad (12)$$

In Expression (12), the first term of the left side corresponds to the ratio of the third intensity signal $S_{o3}$ and fourth intensity signal $S_{o4}$ which are acquired by the signal acquiring section 32. The values of $I_{03}$ and $I_{04}$ are already known, and therefore the second term of the left side is constant. When first and second light beams are selected as two beams for which the extinction coefficients of the blood in a state where the oxygen saturation is 100% are substantially equal to each other, namely, it is possible to offset influences on extinction due to the arterial blood and the tissue relating to the third and fourth light beams.

From Expressions (6) and (12), moreover, the following expression is obtained:

$$[\ln(I_4/I_3) - \ln(I_{04}/I_{03})]/[\ln(I_2/I_1) - \ln(I_{02}/I_{01})] = (E_{v3} - E_{v4})/(E_{v1} - E_{v2}) \quad (13)$$

When two sets of two light beams for which the extinction coefficients of the blood in a state where the oxygen saturation is 100% are substantially equal to each other are used, namely, it is possible to offset influences on extinction due to at least one of the thickness variation of the venous blood and the variation of the hemoglobin concentration in blood. The venous oxygen saturation of the subject may be expressed as the function of the right side of Expression (13).

When instructions stored in the memory 332 are executed by the processor 331, the medical photometer 30 calculates the venous oxygen saturation in a state where the arterial oxygen saturation of the subject is 100%, based on the first control signal $S_{i1}$, the second control signal $S_{i2}$, the third control signal $S_{i3}$, the fourth control signal $S_{i4}$, the first intensity signal $S_{o1}$, the second intensity signal $S_{o2}$, the third intensity signal $S_{o3}$, and the fourth intensity signal $S_{o4}$.

According to the configuration, even when the arterial oxygen saturation of a subject is 100%, it is possible to determine whether the amount of administration of oxygen to the subject is adequate, based on the calculated venous oxygen saturation. In other words, a novel index is provided which, when the arterial oxygen saturation of a subject is 100%, enables to determine whether the amount of administration of oxygen to the subject is adequate.

Although not illustrated, the medical photometer 30 includes a notifying section. The notifying section notifies the user of the calculated venous oxygen saturation by using at least one of visual notification, audible notification, and haptic notification. The notifying section may be configured so as to perform the notification only in the case where the calculated venous oxygen saturation suggests excessive administration of oxygen to the subject.

As illustrated by the broken line in FIG. 1, the medical photometer 30 may be connected to an oxygen administration apparatus 40 with wire or wireless connection. The oxygen administration apparatus 40 is an apparatus for administrating oxygen to the subject. In this case, the medical photometer 30 may cause the signal producing section 31 to produce a control signal S which controls the operation of the oxygen administration apparatus 40, based on the calculated venous oxygen saturation.

In the case where the calculated venous oxygen saturation suggests insufficient administration of oxygen, for example, the signal producing section 31 is caused to produce a control signal which controls the oxygen administration apparatus 40 so as to increase the amount of administration of oxygen. In the case where the calculated venous oxygen saturation suggests excessive administration of oxygen, the signal producing section 31 is caused to produce a control signal which controls the oxygen administration apparatus 40 so as to decrease the amount of administration of oxygen.

According to the configuration, adequate administration of oxygen under a situation where the arterial oxygen saturation of a subject is 100% can be automated.

JP-A-2014-147473 discloses a technique in which an influence on extinction due to the tissue of the subject in calculation of the arterial oxygen saturation is eliminated by pressurizing the tissue to evacuate the blood. Specifically, the tissue of the subject is irradiated by first and second light beams of different wavelengths. In a first state where the tissue is not pressurized, received light intensities of the first and second light beams are acquired. In a second state where the tissue is pressurized, then, received light intensities of the first and second light beams are acquired. A first light attenuation is acquired from the received light intensity of the first light beam which is acquired in the first state, and that of the first light beam which is acquired in the second state. A second light attenuation is acquired from the received light intensity of the second light beam which is acquired in the first state, and that of the second light beam which is acquired in the second state. The arterial oxygen saturation of the subject is calculated based on the difference between the first light attenuation and the second light attenuation.

Referring to the technique, Expressions (1), (2), (7), and (8) may be rewritten respectively as follows:

$$A_1 = \ln(I_{21}/I_{11}) \quad (14)$$

$$A_2 = \ln(I_{22}/I_{12}) \quad (15)$$

$$A_3 = \ln(I_{23}/I_{13}) \quad (16)$$

$$A_4 = \ln(I_{24}/I_{14}) \quad (17)$$

In the above, $I_{11}$, $I_{12}$, $I_{13}$, and $I_{14}$ indicate the intensities of the first, second, third, and fourth light beams which are acquired by the light detector 20 in a first state, respectively, and $I_{21}$, $I_{22}$, $I_{23}$, and $I_{24}$ indicate the intensities of the first, second, third, and fourth light beams which are acquired by the light detector 20 in a second state, respectively. The first state corresponds to a state where the tissue of the subject is not pressurized. The second state corresponds to a state where the tissue of the subject is pressurized.

Expression (18) is obtained based on the description referring to Expressions (3) to (6). Similarly, Expression (19) is obtained based on the description referring to Expressions (9) to (12).

$$\ln(I_{12}/I_{11}) - \ln(I_{22}/I_{21}) = (E_{v1} - E_{v2}) Hb \cdot D_v \quad (18)$$

$$\ln(I_{14}/I_{13}) - \ln(I_{24}/I_{23}) = (E_{v1} - E_{v2}) Hb \cdot D_v \quad (19)$$

Then, the following expression is obtained based on the description referring to Expression (13):

$$[\ln(I_{14}/I_{13}) - \ln(I_{24}/I_{23})]/[\ln(I_{12}/I_{11}) - \ln(I_{22}/I_{21})] = (E_{v3} - E_{v4})/(E_{v1} - E_{v2}) \quad (20)$$

The intensity $I_{11}$ of the first light beam, intensity $I_{12}$ of the second light beam, intensity $I_{13}$ of the third light beam, and intensity $I_{14}$ of the fourth light beam which are acquired by the light detector 20 in the first state correspond to the first intensity signal $S_{o1}$, the second intensity signal $S_{o2}$, the third intensity signal $S_{o3}$, and the fourth intensity signal $S_{o4}$ which are acquired from the light detector 20 in the first state, respectively. The intensity $I_{21}$ of the first light beam, intensity $I_{22}$ of the second light beam, intensity $I_{23}$ of the third light beam, and intensity $I_{24}$ of the fourth light beam which are acquired by the light detector 20 in the second state correspond to the first intensity signal $S_{o1}$, the second intensity signal $S_{o2}$, the third intensity signal $S_{o3}$, and the fourth intensity signal $S_{o4}$ which are acquired from the light detector 20 in the second state, respectively.

Figure 3:
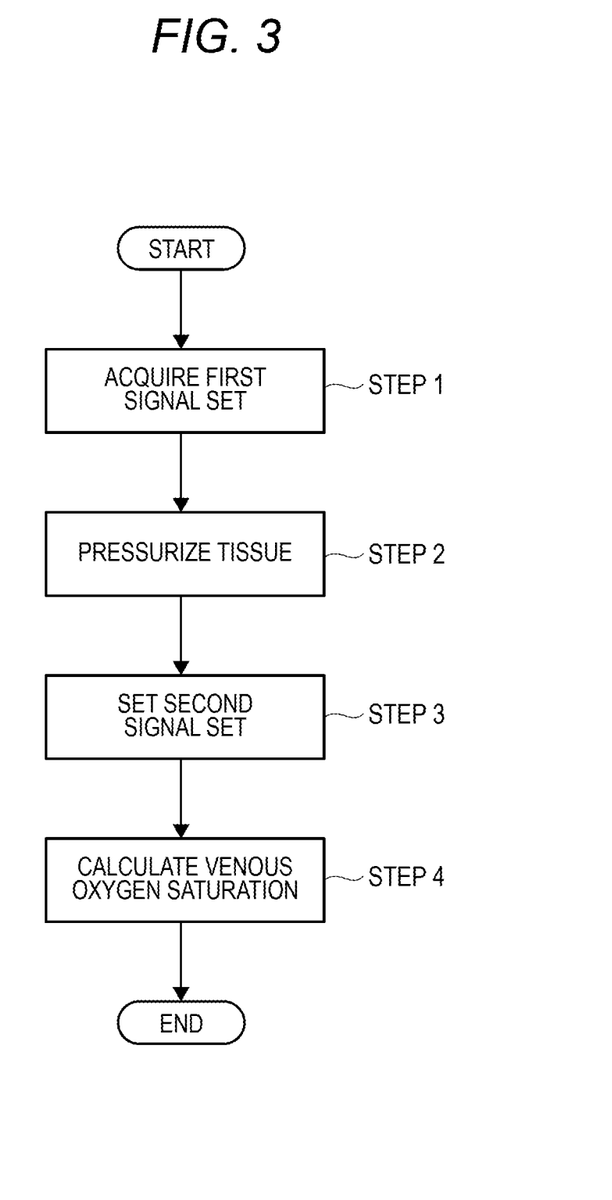
FIG. 3 is a flowchart illustrating an operation example of a medical photometer in FIG. 1.

Therefore, the venous oxygen saturation in a state where the arterial oxygen saturation of the subject is 100% may be calculated based on: a first signal set including the first intensity signal $S_{o1}$, the second intensity signal $S_{o2}$, the third intensity signal $S_{o3}$, and the fourth intensity signal $S_{o4}$ which are acquired in the first state; and a second signal set including the first intensity signal $S_{o1}$, the second intensity signal $S_{o2}$, the third intensity signal $S_{o3}$, and the fourth intensity signal $S_{o4}$ which are acquired in the second state. FIG. 3 illustrates an example of the operation of the medical photometer 30 which is based on the technique.

In the state where the tissue is not pressurized, firstly, the first signal set including the first intensity signal $S_{o1}$, the second intensity signal $S_{o2}$, the third intensity signal $S_{o3}$, and the fourth intensity signal $S_{o4}$ is acquired (STEP 1).

Then, the tissue is pressurized (STEP 2). The pressurization may be performed by the hand of the user, or by a cuff In the case where the pressurization is performed by the hand of the user, it is preferable to notify the user of the timing of the pressurization by using at least one of visual notification, audible notification, and haptic notification. The notification may function as a trigger for the medical photometer 30 to acquire the second signal set. Alternatively, the user may input the timing of pressurization to the medical photometer 30 by operating a button or the like.

In the case where the pressurization is performed by a cuff, the medical photometer 30 may include a pressure controller which controls the internal pressure of the cuff. The pressure controller may include a pump. The operation of the pressure controller may be controlled by the controller 33. The pressurization by the cuff may be performed in response to, for example, a button operation conducted by the user, or automatically by the controller 33.

In the state where the tissue is pressurized, the second signal set including the first intensity signal $S_{o1}$, the second intensity signal $S_{o2}$, the third intensity signal $S_{o3}$, and the fourth intensity signal $S_{o4}$ is acquired (STEP 3).

Then, the venous oxygen saturation in a state where the arterial oxygen saturation of the subject is 100% is calculated based on the acquired first and second signal sets (STEP 4).

According to the configuration, simply by changing the pressurization state of the tissue, the venous oxygen saturation in a state where the arterial oxygen saturation of the subject is 100% may be calculated based on only the first intensity signal $S_{o1}$, the second intensity signal $S_{o2}$, the third intensity signal $S_{o3}$, and the fourth intensity signal $S_{o4}$ which are acquired from the light detector 20. Even when the arterial oxygen saturation of a subject is 100%, namely, it is possible to determine whether the amount of administration of oxygen to the subject is adequate, based on the calculated venous oxygen saturation.

In the example, the state where the tissue is not pressurized corresponds to the first signal set, and the state where the tissue is pressurized corresponds to the second signal set. Alternatively, the state where the tissue is pressurized may correspond to the first signal set, and the state where the tissue is not pressurized may correspond to the second signal set.

The above-described embodiment is a mere example for facilitating understanding of the presently disclosed subject matter. The configuration of the embodiment may be adequately changed or improved without departing from the spirit of the presently disclosed subject matter. It is obvious that equivalents are included within the technical scope of the presently disclosed subject matter.

In the above-described embodiment, 660 nm and 700 nm are selected as the set of the first wavelength $\lambda_1$ and the second wavelength $\lambda_2$, and 645 nm and 730 nm are selected as the set of the third wavelength $\lambda_3$ and the fourth wavelength $\lambda_4$. However, at least one of the two sets may be changed to arbitrary two wavelengths at which the extinction coefficients of the blood in a state where the oxygen saturation is 100% are substantially equal to each other.

Only the configuration for calculating the venous oxygen saturation of a subject is disposed in the above-described embodiment. However, a configuration for calculating the arterial oxygen saturation of the subject may be disposed. In this case, at least one of components (light emitters, a light detector, a signal producing section, a signal acquiring section, a controller, and the like) may be shared with a corresponding component in the embodiment and for calculating the venous oxygen saturation. The value of the calculated arterial oxygen saturation may be used for determining insufficient administration of oxygen to the subject.

What is claimed is:

1. A medical photometry method, comprising:
    emitting, onto a subject, by a first light emitter a first light beam having a first wavelength selected to correspond to an extinction coefficient of an arterial blood that has a first value in a state where an oxygen saturation of the arterial blood is 100%;
    emitting, onto the subject, by a second light emitter a second light beam having a second wavelength different from the first wavelength and selected to correspond to the extinction coefficient of the arterial blood that has the first value;
    emitting, onto the subject, by a third light emitter a third light beam having a third wavelength selected to correspond to the extinction coefficient of the arterial blood that has a second value in the state where the oxygen saturation of the arterial blood is 100%, the second value being different from the first value;
    emitting, onto the subject, by a fourth light emitter a fourth light beam having a fourth wavelength different from the third wavelength and selected to correspond to the extinction coefficient of the arterial blood that has the second value;
    detecting by a light detector outputs of a first intensity signal corresponding to an intensity of the first light beam having been transmitted through or reflected from tissue of the subject, a second intensity signal corresponding to an intensity of the second light beam having been transmitted through or reflected from the tissue, a third intensity signal corresponding to an intensity of the third light beam having been transmitted through or reflected from the tissue, and a fourth intensity signal corresponding to an intensity of the fourth light beam having been transmitted through or reflected from the tissue; and generating by a medical photometer to which the first light emitter, the second light emitter, the third light emitter, the fourth light emitter, and the light detector are connected with wire or wirelessly, a first control signal that causes the first light emitter to emit the first light beam, a second control signal that causes the second light emitter to emit the second light beam, a third control signal that causes the third light emitter to emit the third light beam, and a fourth control signal that causes the fourth light emitter to emit the fourth light beam;

obtaining by the medical photometer, from the light detector, the first intensity signal, the second intensity signal, the third intensity signal, and the fourth intensity signal; and calculating by the medical photometer a venous oxygen saturation in a state where an arterial oxygen saturation of the subject is 100% based on a value of an intensity of the first light beam emitted from the first light emitter, a value of an intensity of the second light beam emitted from the second light emitter, a value of an intensity of the third light beam emitted from the third light emitter, a value of an intensity of the fourth light beam emitted by the fourth light emitter, a value of the first intensity signal, a value of the second intensity signal, a value of the third intensity signal, and a value of the fourth intensity signal.

2. The medical photometry method according to claim 1, wherein the first wavelength is 660 nm,
the second wavelength is 700 nm,
the third wavelength is 645 nm, and
the fourth wavelength is 730 nm.

3. The medical photometry method according to claim 1, wherein, in the calculating the venous oxygen saturation comprises:

calculating a first parameter related to the venous oxygen saturation based on the value of the first intensity of the first light emitted from the first light emitter, the value of the second intensity of the second light emitted from the second light emitter, the value of the first intensity signal, and the value of the second intensity signal, calculating a second parameter related to the venous oxygen saturation based on the value of the third intensity of the third light emitted from the third light emitter, the value of the fourth intensity of the fourth light emitted from the fourth light emitter, the value of the third intensity signal, and the value of the fourth intensity signal, and calculating the venous oxygen saturation as a ratio of the second parameter to the first parameter.

4. The medical photometry method according to claim 1, wherein the venous oxygen saturation=$[\ln(I_{o4}/I_{o3})]/[\ln(I_2/I_1)-\ln(I_{o2}/I_{o1})]$;

wherein $I_1$ is the value of the first intensity signal, $I_2$ is the value of the second intensity signal, $I_3$ is the value of the third intensity signal, $I_4$ is the value of the fourth intensity signal, $I_{o1}$ is the value of the first intensity of the first light emitted from the first light emitter, $I_{o2}$ is the value of the second intensity of the second light emitted from the second light emitter, $I_{o3}$ is the value of the third intensity of the third light emitted from the third light emitter, and $I_{o4}$ is the value of the fourth intensity of the fourth light emitted from the fourth light emitter.

* * * * *